United States Patent [19]

Rinehart, Jr.

[11] Patent Number: 4,493,796

[45] Date of Patent: Jan. 15, 1985

[54] DIDEMNINS A, B, C, AND DERIVATIVES THEREOF, AS ANTIVIRAL AGENTS

[75] Inventor: Kenneth L. Rinehart, Jr., Urbana, Ill.

[73] Assignee: Board of Trustees, Univ. of Ill., Urbana, Ill.

[21] Appl. No.: 589,199

[22] Filed: Mar. 13, 1984

Related U.S. Application Data

[63] Continuation-in-part of Ser. No. 461,346, Jan. 27, 1983, which is a continuation-in-part of Ser. No. 217,768, Dec. 18, 1980, , which is a continuation-in-part of Ser. No. 186,932, Sep. 12, 1980, abandoned.

[51] Int. Cl.$^3$ .......................................... C07C 103/52
[52] U.S. Cl. ............................................ 260/112.5 R
[58] Field of Search ................................. 260/112.5 R

[56] References Cited

PUBLICATIONS

The Journal of Antibiotics, vol. 23, No. 5, pp. 263–265.

Primary Examiner—Delbert R. Phillips
Attorney, Agent, or Firm—Lawrence T. Welch

[57] ABSTRACT

Novel antibiotics didemnins A, B, C, D, and E (didemnins), are obtained from a marine organism. These antibiotics, and derivatives thereof, are active against a variety of DNA and RNA viruses; thus, they can be used in various environments to control or eradicate these viruses.

14 Claims, 2 Drawing Figures

DIDEMNINS A, B, C, AND DERIVATIVES THEREOF, AS ANTIVIRAL AGENTS

DESCRIPTION

CROSS REFERENCE TO RELATED APPLICATION

This application is a continuation-in-part of copending application Ser. No. 461,346, filed Jan. 27, 1983, which was a continuation-in-part of application Ser. No. 217,768, filed on Dec. 18, 1980, which was a continuation-in-part of application Ser. No. 186,932, filed on Sept. 12, 1980, now abandoned.

BRIEF SUMMARY OF THE INVENTION

Novel antibiotics didemnin A, didemnin B, didemnin C, didemnin D, and didemnin E are extracted from a readily available marine tunicate of the family Didemnidae, and tentatively identified as a Trididemnum sp. These antibiotics are active against DNA viruses, for example, herpes simplex virus types 1 and 2, and vaccinia virus; RNA viruses, for example, coxsackie virus and equine rhinovirus; and P388 leukemia in mice. Thus, these antibiotics can be used to treat infections in humans, animals and plants caused by these viruses and other DNA and RNA viruses. Didemnin A and didemnin B also inhibit L1210 mouse leukemia cells in vitro. Acid addition salts and acyl derivatives of the didemnins can be made and used for the same biological purposes as the parent compounds.

Didemnin D and didemnin E inhibit L1210 mouse leukemia cells in vitro and P388 leukemia in mice. Thus they can be used to treat neoplastic diseases in animals and humans. Acid addition salts and acyl derivatives of didemnins D and E are also part of this invention and are used for the same biological purposes as the parent compounds.

Also included in this invention are the didemnin derivatives, methylene didemnin A, dihydrodidemnin A, N-acetyldidemnin A and diacetyldidemnins A and B, N-propionyl-didemnin A, N-(L)-leucyl didemnin A, and N-(L-prolyl) didemnin A.

Methylene didemnin A inhibits the growth of L1210 leukemia cells in culture and reduces the yield of virus from infected Vero cells. Dihydrodidemnin A is active in vitro against L1210 cells. The N-acetyl derivative of didemnin A is much more active than didemnin A against L1210 cells while diacetyldidemnin A has a better therapeutic ratio in the virus yield assay than does didemnin A.

DETAILED DESCRIPTION OF THE INVENTION

Figure 1:
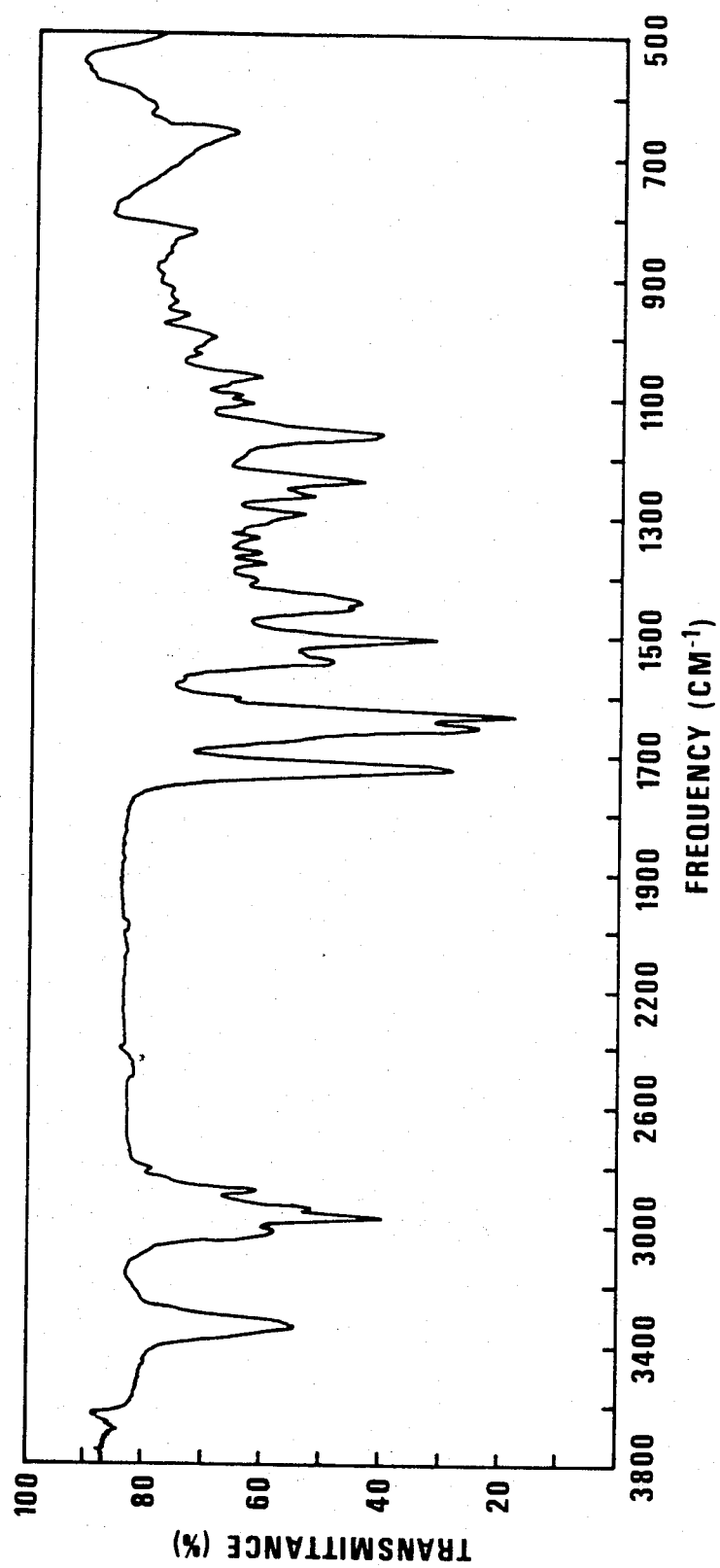

The present invention particularly provides a didemnin of the Formula I wherein R is
(a) hydrogen,
(b) —COCH$_3$,
(c) a side chain of Formula II,
(d) a side chain of Formula III,
(e) CH$_3$CHOHC(O)—,
(f) a side chain of Formula IV,
(g) a side chain of Formula V,
(h) CH$_3$CH$_2$C(O)—,
(i) (CH$_3$)$_2$CHCH$_2$CHCNH$_2$)C(O)—, or
(j) a side chain of formula VI;
wherein R$_1$ is hydrogen; or R and R$_1$ taken together form methylene (—CH$_2$—); wherein R$_2$ is
(a) hydrogen, or
(b) —COCH$_3$; and
wherein X is
(a) =O, or
(b) H, —OH,
or an acylate thereof.

THE ORGANISM

The organism from which the didemnins are extracted is a colonial marine tunicate of the family Didemnidae, Trididemnum sp. These known organisms are in the suborder Aplousobranchia of the order Enterogona of the class Ascidiacea of the subphylum Urochordata of the phylum Chordata. They can be readily obtained by scuba techniques at depths of 10 to 100 feet where they encrust rocks, sponges, gorgonians, etc., in colony sizes up to 3 feet in diameter and ½ inch in thickness. They vary in color depending on location from green-white to purple-white to brown-white to orange-white.

Specific locations from which these organisms have been obtained are as follows:

(1) Southwest side of Long Cay, Lighthouse Reef, Belize, 17° 11.8' N by 87° 36.5' W at a depth of 50 to 100 feet;

(2) Rada el Cove, Isla San Andres, Colombia, 12° 31' 46" N by 81° 44' 5" W at 25 to 33 feet;

(3) Palancar Reef, Isla de Cozumel, Mexico, 20° 18.2' N by 87° 2.5' W at 60 to 100 feet;

(4) On the west side of the southern tip of Turneffe Island, Belize, 17° 11.3' N by 87° 55.6' W at 50 to 75 feet;

(5) Punta Oeste, Coxen's Hole Harbor, Isla Roatan, Honduras, 16° 15' N by 86° 38' W at 10 to 70 feet;

(6) On the leeward side of the western-most Holandes Cay, Isla San Blas, Panama, 9° 35.6' N by 78° 47' W at 60 feet.

INSTRUMENTATION, MATERIALS AND METHODS

Melting points were determined on a Kofler Micro-hot stage apparatus and are uncorrected. Optical rotations were measured on a Rudolph Research Autopol III automatic polarimeter with a 1 dm cell using dichloromethane as solvent. Proton magnetic resonance ($^1$H NMR) spectra were determined on Nicolet Instrument Corp. NT-360 and Varian XL-200 spectrometers with chloroform-d as solvent and a deuterium lock. Chemical shifts are reported in parts per million (ppm) downfield from tetramethylsilane (TMS) as internal standard.

Low resolution electron ionization (EI) mass spectra were recorded on a Varian MAT mass spectrometer, model CH-5 DF. Gas chromatography/mass spectrometry (GC/MS) samples (for confirmation of GC amino acid analysis) were analyzed on a VG Micromass 7070 mass spectrometer coupled to a Varian model 3700 gas chromatograph. High resolution electron ionization mass spectrometry (HREIMS) and high resolution fast atom bombardment mass spectrometry (HRFABMS) samples were analyzed on a Finnigan MAT 731 mass spectrometer. Low resolution fast atom bombardment (FAB) mass spectra were recorded on the VG 7070 or the Finnigan MAT 731.

Gas chromatography (GC) employed a Varian model 3700 gas chromatograph with a 6 ft×2 mm i.d. helical glass column of 3% OV-17 on 100/120 Gas-Chrom-Q (conditions: carrier gas (He) flow rate 35 ml/min; temperature programmed from 60°–260° C. at 10° C./min).

The compositions of all chromatographic solvents used are expressed as volume:volume ratios. Thin-layer chromatography (TLC) was carried out on precoated glass plates (0.25 mm, silica gel 60 F-254, Merck) using 9:1 chloroform:methanol as eluent unless otherwise stated. All Rf values are reported in this solvent system unless otherwise stated. Spots were visualized by exposure to iodine vapors. High performance liquid chromatography (HPLC) utilized a Waters Associates solvent delivery system (model 6000A), a Water Associates model R401 refractive index detector, and an Altex ODS ($5\mu$. 1–0 mm i.d.) reversed phase semipreparative column at a flow rate of 2.5 ml/min. The most common solvent used was 77:23:0.01 methanol:water:triethylamine, buffered to pH 7.5 with acetic acid. This system is designated solvent system A. Preparative liquid chromatography (Prep LC) employed a Waters Associates Prep 500A solvent delivery system with PrepPak 500 silica or ODS cartridges at a flow rate of 200 ml/min. Isocratic runs made use of a built-in refractive index detector.

A variety of methods can be used to isolate and purify the didemnins from samples of the tunicate organism, for example, solvent extraction, partition chromatography, silica gel chromatography, liquid-liquid distribution in a Craig apparatus, adsorption on resins, and crystallization from solvents.

The following examples describe preferred processes, but are not to be construed as limiting.

ISOLATION AND PURIFICATION OF DIDEMNINS A, B AND C

EXAMPLE 1

Tunicate sample AHCE #614 was collected on the southwest side of Long Cay, Lighthouse Reef, Belize, 17° 11.8' N by 87° 36.5' W at a depth of 50 to 100 feet. The sample was placed in isopropanol and stored at −10° C. until it was extracted by the following procedure.

A sample of tunicate (500 g) was homogenized in a Waring blender with a total of 2.4 liters of 3:1 MeOH:toluene and the residue was filtered with suction to give a dark olive green solution. Aqueous isopropanol (500 ml) from the storage container was evaporated to ~40 ml of a mostly aqueous, oily solution. This material was suspended in 400 ml of 3:1 methanol:toluene and combined with the 2.4 liters above.

The resulting dark green solution was partitioned versus 1400 ml of 1N NaNO$_3$ solution to give an aqueous phase and a toluene phase. The aqueous phase was extracted with chloroform (1×500 ml, 1×300 ml, 2×250 ml and 1×100 ml) to give a cloudy grass green chloroform solution which was evaporated under reduced pressure, taken up in dry CHCl$_3$, and filtered to remove salt. Evaporation of the chloroform yielded 878 mg of a dark green flaky solid.

This material (108 mg) was loaded onto a silica gel (Brinkmann, particle size 0.05–0.2 mm) column of dimensions 1.7 cm×46 cm, which was packed in chloroform. The column was eluted in step gradient fashion with 150 ml CHCl$_3$, 150 ml CHCl$_3$:MeOH, 99:1, 150 ml CHCl$_3$:MeOH, 97:3; and 250 ml CHCl$_3$:MeOH, 95:5. Three-ml fractions were collected, and the content of each fraction was evaluated by thin-layer chromatography, developing with 9:1 CHCl$_3$:MeOH.

Relatively impure didemnin C (Rf 0.66–0.72) was obtained as an oil in trace amounts as the first major non-pigment to elute. It was contained in the last 30 ml of the 3% methanol in chloroform wash. Essentially pure didemnin C can be obtained by use of preparative thin-layer chromatography, as described for preparing didemnin A, below. Essentially pure didemnin B (Rf 0.59–0.64) was obtained as a yellow-white amorphous solid (6.1 mg). In most cases, didemnin B was already pure enough (by TLC) for data accumulation and testing. Didemnin A (Rf 0.46–0.52) was obtained as a greenish-white solid (34.7 mg) containing substantial impurities of both higher and lower Rf. Didemnins B and A were contained in the first 100 ml of the 5% methanol in chloroform wash. When an essentially pure sample was desired (for mass spectrometry, etc.), didemnin A was purified by preparative thin-layer chromatography on 0.25 mm TLC plates employing 9:1 CHCl$_3$:MeOH as the eluent. In many cases, the best fractions of didemnin A collected from later columns had fewer impurities, which allowed immediate use for reactions and spectral data accumulation.

EXAMPLE 2

Isolation, Purification and Physical Characterization of Didemnins D and E (see Chart I for structures)

A variety of methods can be used to isolate and purify the didemnins and nordidemnins from samples of the tunicate organism, for example, solvent extraction, partition chromatography, silica gel chromatography, liquid-liquid distribution in a Craig apparatus, adsorption on resins, and crystallization from solvents.

The following examples describe preferred processes, but are not to be construed as limiting.

A sample of tunicate (500 g), stored at −10° C. since collection, along with the residue from evaporation of a proportionate amount of the ethanol or isopropanol in which it was stored, was homogenized in a Waring blender with 1600 ml of 3:1 methanol:toluene. The mixture was filtered and the filtrate was partitioned with 800 ml of 1N NaNO$_3$. The aqueous phase was collected and extracted with a total of 600 ml of dichloromethane (300, 200, 100 ml). Evaporation of the dried (Na$_2$SO$_4$) combined dichloromethane extracts gave 0.88 g (0.18%) of a dark green chunky solid. This material was subjected to preparative LC eluting progressively with 1 L of chloroform, 1 L of 99:1 chloroform:methanol, and 2 L of 97:3 chloroform:methanol, and collecting 90 ml fractions. The prep LC cartridge was then washed with 1 L of 60:40 chloroform:methanol. The fractions were examined by TLC. Impure didemnin C (Rf 0.69) was obtained as a yellow oil in trace amounts as the first non-pigment to elute. Impure didemnin B (Rf 01.62) was obtained next as a dark yellow amorphous solid. Impure didemnin A (Rf 0.49) was obtained as a greenish-yellow solid contaminated by lower homologs as evidenced by mass spectral analysis of the mixtures and by GC/MS analysis of their derivatized hydrolysates (see below). Didemnins A-C and their homologs could be separated from each other and from the pigments by reversed phase HPLC using 77:23:0.01 methanol:water:triethylamine buffered to pH 7.5 with acetic acid (solvent system A). Didemnins obtained through this procedure were cleansed of triethylammonium acetate by dissolving in dichloromethane, extracting with water, and drying (Na$_2$SO$_4$) and evaporating the organic phase. In cases where no didemnin A (or any of its homologs) was present in the sample, no buffer was necessary and 77:23 methanol:water was used for HPLC separation of the didemnins.

The 60:40 chloroform:methanol from the prep LC run above was evaporated, dissolved in dichloromethane, filtered and reevaporated prior to further chromatography. The resulting dark green oil was subjected to reversed phase HPLC using 73:27 methanol:water to afford didemnins D (Rf 0.05) and E (Rf 0.18).

Total overall yields of didemnins A-E were: didemnin A, 236 mg (0.047% of wet weight); didemnin B, 41.6 mg (0.008%); didemnin C, 4.2 mg (0.0008%), didemnin D, 20.2 mg (0.004%); didemnin E, 33.6 mg (0.007%).

A similar isolation scheme was employed later during large scale production of didemnin B for biological testing. The dichloromethane extract was obtained as before with only minor modifications due to scale-up. Prep LC employed an isocratic chloroform:methanol solvent system ranging from 98:2 to 96:4 depending on the condition of the reusable PrepPak cartridge. This allowed the use of the built-in refractive index detector to monitor elution of the didemnins. Fractions obtained through this procedure were chromatographed on a reversed phase (ODS) PrepPak cartridge with 77:23 methanol:water, again monitoring with the refractive index detector. Pooling of the appropriate fractions gave yields of didemnins A-C similar to those obtained with the original procedure. Didemnins D and E could only be separated by HPLC as above.

EXAMPLE 3

Salts of Didemnins

Since the didemnins are weakly basic, they form salts with mineral acids such as HCl, $H_2SO_4$, $H_3PO_4$, and the like. Such salts can be prepared by suspending the didemnins in water, adding a dilute acid until the pH of the solution is about 3 to 4, and freeze-drying the solution to provide a dried residue of the didemnin salt. Salts of the didemnins can be used for the same biological purposes as the parent compounds.

EXAMPLE 4

Derivatives of Didemnins

The didemnins have free amino and hydroxyl groups available for derivatization. Thus, acyl amides and esters of the didemnins can be prepared by use of standard acylating conditions well known to those skilled in the art. Acyl derivatives of the didemnins can be used for the same biological purposes as the parent compounds.

Acids which can be used in the acylation of a didemnin include (a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropiolic acid and naphthylacetic acid, and the like. Suitable halo-, nitro-, hydroxy-, keto-, amino-, cyano-, thiocyano-, and lower alkoxyhydrocarbon carboxylic acids include hydrocarboncarboxylic acids as given above which are substituted by one or more of halogen, nitro, hydroxy, keto, amino, cyano, or thiocyano, or lower alkoxy, advantageously lower alkoxy of not more than six carbon atoms, for example, methoxy, ethoxy, propoxy, butoxy, amyloxy, hexyloxy, and isomeric forms thereof. Examples of such substituted hydrocarbon carboxylic acids are:

mono-, di-, and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicylic acid;
p-hydroxybenzoic acid;
β-resorcylic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);
malic acid;
citric acid;
isocitric acid;
6-methylsalicylic acid;
mandelic acid;
levulinic acid;
pyruvic acid;
glycine;
alanine;
valine;
isoleucine;
leucine;
phenylalanine;

proline;
serine;
threonine;
tyrosine;
hydroxyproline;
ornithine;
lysine;
arginine;
histidine;
hydroxylysine;
phenylglycine;
p-aminobenzoic acid;
m-aminobenzoic acid;
anthranilic acid;
aspartic acid;
glutamic acid;
aminoadipic acid;
glutamine;
asparagine;
and the like.

EXAMPLE 5

Diacetyldidemnin A (see Chart I for structure)

A sample of didemnin A (20 mg) was dissolved in 2 ml of pyridine and 1 ml of acetic anhydride was added. The solution was stirred at room temperature for 18 hours and then evaporated to dryness. The residue obtained was dissolved in 8 ml of ether and extracted with water (3×3 ml). Evaporation of the dried ($Na_2SO_4$) organic phase afforded 18 mg (83% yield) of diacetyldidemnin A as a white amorphous solid; mp 117°–119° C.; Rf 0.65; HPLC retention time (solvent system A) 28.5 min; $^1$H NMR (200 MHz, $CDCl_3$) spectrum contains resonances for acetyl methyl groups at 1.9 and 2.1 ppm, a downfield-shifted N-methyl group at 2.8 ppm, a downfield-shifted CH-N proton at 5.1 ppm, and a downfield-shifted CH-O proton at 5.3 ppm. EIMS (70 eV) shows major ions at m/z 70 (46% of base peak), 77 (3), 83 (6), 86 (14), 91 (3), 98 (4), 100 (34), 113 (4), 114 (6), 121 (53), 124 (12), 125 (6), 134 (7), 142 (25), 154 (16), 170 (38), 178 (8), 192 (4), 225 (14), 253 (3), 262 (10), 288 (2), 307 (4), 383 (2); HREIMS gave a molecular ion at m/z 1026.5895, which corresponds to the expected molecular formula $C_{53}H_{82}N_6O_{14}$ ($\Delta=0.7$ mmu).

EXAMPLE 6

Diacetyldidemnin B (see Chart I for structure)

A sample of didemnin B (1.0 mg) was dissolved in 1 ml of pyridine and 0.5 ml of acetic anhydride was added. The solution was stirred at room temperature for 18 hours and evaporated to dryness. The residue obtained was dissolved in 3 ml of ether and extracted with water (4×1.5 ml). Evaporation of the dried ($Na_2SO_4$) organic phase afforded 0.90 mg (84% yield) of diacetyldidemnin B as a white, amorphous solid, mp 128°–131° C.; Rf 0.65; HPLC retention time (84:16 methanol:water) 9.1 min; EIMS (70 eV) major ions at m/z 70 (100% of base peak), 86 (12), 100 (13), 121 (45), 154 (18), 184 (15), 212 (20), 224 (4), 268 (9), 339 (9), 422 (3); HREIMS gave a molecular ion at m/z 1195.6604 which corresponds to the expected molecular formula $C_{61}H_{93}N_7O_{17}$ ($\Delta=-2.2$ mmu).

EXAMPLE 7

N-Acetyldidemnin A (see Chart I for structure)

A sample of didemnin A (22 mg) was dissolved in 2 ml of pyridine. A solution of 22 μl (24 mg) of acetic anhydride in 1.0 ml of pyridine was made up and 110 μl of this solution (a 10% excess) was added to the didemnin A solution. The reaction mixture was stirred at room temperature for 24 hours and then evaporated to dryness. The residue was dissolved in 8 ml of ether and extracted with water (3×3 ml). Evaporation of the dried ($Na_2SO_4$) organic phase afforded 21 mg of a mixture of N-acetyldidemnin A and unreacted didemnin A. Separation of these components by HPLC (77:23 methanol:water) gave pure N-acetyldidemnin A (15 mg; 65% yield) as a white, amorphous solid which has: HPLC retention time 22.6 min; mp 124°–126° C.; Rf 0.55; $^1$H NMR (360 MHz, $CDCl_3$) resonances for an acetyl methyl group at 2.2 ppm, a downfield-shifted N-methyl group at 2.9 ppm, and a downfield-shifted CH-N proton at 5.1 ppm; FABMS major positive ions at m/z 86 (18% of base peak), 100 (32), 121 (7), 142 (18), 164 (10), 170 (29), 210 (5), 228 (5), 307 (12), 734 (47), 816 (31), 943 (28), and 985 (100, M+H).

When this reaction was run on a larger scale, again using a 10% excess of acetic anhydride, HPLC was not always necessary, in which case a much better yield (ca. 85%) was obtained.

EXAMPLE 8

Dihydrodidemnin A (see Chart I for structure)

A sample of didemnin A (50 mg) was dissolved in 3 ml of ethanol and a solution of 5 mg of sodium borohydride in 5 ml ethanol was added. The solution was stirred at room temperature while the appearance of product was monitored by TLC. The reaction was halted after 4 hours (does not go to completion). Unreacted sodium borohydride was destroyed by addition of 2% HCl until evolution of hydrogen ceased. The solvent was evaporated and the residue suspended in 5 ml of water. This suspension was extracted with 12 ml of dichloromethane (3×4 ml) and the combined organic phases were dried over sodium sulfate, filtered, and evaporated to give 40 mg of a colorless oil. The desired product could be obtained from this oil by prep TLC in 9:1 chloroform:methanol or by reversed phase HPLC (solvent system A), either method giving a yield of 12 mg (24%) of dihydrodidemnin A. The compound has: Rf 0.17; mp 124°–127° C.; HPLC retention time (solvent system A) 24.2 min; FABMS (positive ion) ions at m/z 70 (54% of base peak), 86 (53), 100 (55), 114 (57), 121 (63), 164 (78), 192 (21), 208 (22), 210 (24), 226 (23), 307 (34), 418 (10), 544 (3), 552 (2), 560 (2), 574 (2), 692 (11), 818 (2), 945 (100, base peak, M+H).

Hydrolysis, followed by derivatization and GC analysis shows the same amino acid composition as didemnin A. Hydrolysis, followed by extraction with ether and GC analysis shows the presence of dihydroHip (i.e., α,β-dihydro-α-methyl-γ-isopropyltetronic acid).

EXAMPLE 9

Methylene-didemnin A (see Chart I for structure)

A sample of didemnin A (12.5 mg) was dissolved in 0.25 ml of methanol and 25 μl of 37% aqueous formaldehyde solution was added. The solution was stirred for 48 hours at room temperature, evaporated, redissolved in methanol, and filtered through a $C_{18}$ sep-pak (Waters Associates) which had been preconditioned by washing with methanol. The sample was washed through with 1 ml of methanol and the washings were filtered and evaporated to give 12.4 mg (97% yield) of a white, amorphous solid with: mp 134°–136° C.; Rf 0.63; HPLC retention time (solvent system A) 34.8 min; FABMS major positive ions at m/z 70 (100% of base peak), 86 (54), 100 (46), 121 (31), 164 (50), 195 (18), 210 (13), 221 (17), 226 (14), 307 (14), 704 (13), 955 (M+H, 71). The exact mass of the FAB M+H ion was measured by HRFABMS at 955.5698 daltons which is in agreement with the formula $C_{50}H_{79}N_6O_{12}$ ($\Delta$=5.7 mmu).

The $^1$H NMR spectrum (360 MHz, CDCl$_3$) when compared to that of didemnin A showed the absence of an amide proton signal at $\delta$7.8 previously assigned to threonine. The $\alpha$-proton signal of threonine, a doublet of doublets at $\delta$4.9 in didemnin A, was present as a doublet at $\delta$4.9 in the spectrum of methylene didemnin A. The N-methyl and $\alpha$-proton resonances assigned to MeLeu were both shifted slightly upfield. These data, and the presence of two new proton signals ($\delta$4.89, d, 1H and $\delta$2.93, d, 1H) for the new methylene unit, are all consistent with the structure of methylene didemnin A.

EXAMPLE 10

N-Propionyl-Didemnin A

Propionic acid (31 mg) and dicyclohexylcarbodiimide (45 mg) were dissolved in methylene chloride (5 ml) and left at 0° C. for 90 minutes. The Dicyclohexylurea was filtered and the filtrate was added to didemnin A (119 mg). After a further 16 hours at 0° C., the product was blown dry under nitrogen and then purified by reverse phase HPLC (77/23 methanol/water as solvent, at 2.5 ml per minute, using 254 nm UV detection) to give the titled product (134 mg, 64%), $[\alpha]^{25}_D$ −74.8° C. 4.0: chloroform.

Anal. Calcd. for $C_{52}H_{83}N_6O_{13}$ (M+H) mol. wt. 999.608. Found: mol. wt. 999.5985 (M+H: HRFABMS).

EXAMPLE 11

N-(L)-Leucyl-Didemnin A

Benzyloxycarbonyl-leucine (76 mg) and dicyclohexylcarbodiimide (31 mg) were dissolved in methylene chloride (5 ml) at 0° C. After one hour the solid dicyclohexylurea was filtered off and the filtrate was added to didemnin A (140 mg). After 16 hours at 0° C., the solution was blown dry under nitrogen. The solid material exhibited the required mass spectral peak for (N-benzyloxycarbonyl-L-leucyl)didemnin A (1190, M+H). This material was then hydrogenated overnight in methanol (10 ml) over 5% palladium-on-charcoal (71 mg) to give an oil (173 mg). This material was purified by reverse phase HPLC (C-18 semipreparative column 77/23 methanol/water as a solvent, at 2.5 ml/per minute flow rate, detection by UV at 254 nm) to give the titled compound (59 mg, 38%), $[\alpha]^{25}_D$ −66.0° (C=1.4: chloroform).

Anal. Calcd. for $C_{55}H_{90}N_7O_{13}$ (M+H): mol. wt. 1056.6595. Found: Mol. wt., 1056.6590 (M+H: HRFABMS).

EXAMPLE 12

N-(L-Prolyl)-Didemnin A

Benzyloxycarbonyl-L-proline (23 mg) and dicyclohexylcarbodiimide (10 mg) were dissolved in methylene chloride (2 ml) and left at 0° C. for 90 minutes. The dicyclohexylurea was then filtered off and the filtrate added to didmenin A (43 mg). After a further 16 hours at 0° C., the product was blown dry under nitrogen. The FAB mass spectra showed the desired peak for (N-benzyloxycarbonyl-L-prolyl)-didmenin A (1174 M+H). The material (70 mg) was then hydrogenated in methanol (10 ml) with 5% palladium-on-charcoal (25 mg) for 16 hours. After filtration, the crude product (54 mg) was purified by reverse phase HPLC (77/23 methanol/water as a solvent, buffered at pH 7.5 with acetate/triethylamine, 2.5 ml per minute flow, using a 254 nanometer UV detection), to give the titled compound (7 mg: 15%), $[\alpha]^{25}_D$ −47.7° (C 0.35: chloroform).

Anal. Calcd. for $C_{54}H_{86}N_7O_{13}$ (M+H) mol. wt., 1040.6283. Found: Mol. wt., 1040.6250 (M+H: HRFABMS).

Characterization of Didemnins

Solubilities

Didemnins A, B and C are soluble in methanol, ethanol, isopropanol, dioxane, ethyl acetate, and chloroform. They are only sparingly soluble in toluene and insoluble in water.

Acid Hydrolysis of Didemnins

The didemnin samples were hydrolyzed in 6N HCl at 110° C. for 24 hours. The resulting amino acids were identified by field desorption mass spectrometry (FDMS) of the mixture, as well as by gas chromatography (GC)/MS of the amino acids' trifluoroacetyl n-butyl ester derivatives. They were also quantitated by GC, and their identities confirmed by coinjection with derivatives of authentic samples.

Didemnin A contains a mole each of leucine (Leu); N-methylleucine (MeLeu), threonine (Thr); proline (Pro); N,O-dimethyltyrosine (Me$_2$Tyr); and statine (Sta) [see H. Morishima et al., Journal of Antibiotics 23: 263 (1970) for a description of statine (from pepstatin)]. Statine was assigned as the threo isomer by its co-elution with the synthetic R,S-isomer, while gas chromatography on an optically active column indicated Leu, Pro, Thr, and Me$_2$Tyr to have the L-configuration and MeLeu to have the D-configuration.

Didemnin B contains a mole of each of the above six amino acids plus a mole of lactic acid and an additional mole of proline. Didemnin C contains a mole of each of the above six amino acids plus a mole of lactic acid. In addition to the above amino acids, each didemnin contains a hydroxyisovalerylpropionyl (Hip) group.

The order of linkage of these seven units was established by the fragment ions identified in high resolution electron ionization mass spectra.

Mass Spectra

Didemnin A has the following mass spectral peaks: a molecular ion at 942.5678 ($C_{49}H_{78}N_6O_{12}$) and fragments at m/z 886, 843, 800, 756, 611, 583, 557, 523, 501, 499, 480, 455, 401, 383, 356, 313, 310, 298, 288, 262, 210, 183, 178, 154, 139, 134, 128, 122, 121, 100.

The field desorption mass spectrum of didemnin B gives an M+H ion at 1112.6442 ($C_{57}H_{90}N_7O_{15}$). The electron impact mass spectrum of didemnin B contains ions at m/z 942, 924, 913, 886, 844, 843, 797, 756, 611, 593, 557, 523, 425, 396, 383, 313, 307, 288, 262, 224, 210, 184, 154, 121, 100.

The field desorption mass spectrum of didemnin C contains an M+H ion at 1014.5873 ($C_{52}H_{82}N_6O_{14}$). In addition, the mass spectrum of didemnin C obtained by electron ionization gives ions at m/z 958, 887, 859, 842, 693, 675, 578, 547, 536, 494, 368, 283, 262, 237, 224, 200, 172, 154, 121, 100. The minor homolog of didemnin C gives an M+H ion at 1000.5714 ($C_{51}H_{80}N_6O_{14}$). Its electron ionization mass spectrum contains peaks at m/z 944, 873, 845 and 828 indicative of the homology.

NMR Spectra

Didemnin A had the following proton NMR peaks, in ppm from tetramethylsilane: 8.3, 7.8, 7.5, 7.1, 6.9, 5.2, 5.0, 4.9, 4.8, 4.6, 4.2, 4.1, 4.0, 3.8, 3.7, 3.6, 3.4, 3.2, 3.1, 2.9, 2.6 (singlet methyl), 2.6 (doublet of doublets), 2.4 (singlet methyl), 2.4 (multiplet), 2.1, 1.8, 1.6, 1.4, 1.35, 1.30, 1.2, 0.9 (several overlapping methyl doublets).

Didemnin B had the following proton NMR peaks, in ppm from tetramethylsilane: 8.0, 7.8, 7.4, 7.2, 7.0, 5.5, 5.4, 5.3, 4.9, 4.8, 4.6, 4.5, 4.4, 4.2, 3.9, 3.8, 3.5, 3.4, 3.3 (doublet), 3.3 (singlet methyl), 3.1, 2.8, 2.7 (singlet methyl), 2.5, 2.3, 2.1, 1.9, 1.7, 1.5, 1.4, 1.3, 1.0 (several overlapping methyl doublets).

Didemnin C had the following proton NMR peaks, in ppm from tetramethylsilane: 7.7, 7.4, 7.2., 7.0, 5.2, 5.0, 4.8, 4.5, 4.2, 4.0, 3.7, 3.5, 3.3, 3.1, 3.0, 2.9, 2.8 (singlet methyl), 2.4 (singlet methyl), 2.3, 2.2., 2.1, 1.8, 1.5, 1.4–1.25, 1.1–0.8 (several overlapping methyls).

Didemnin A had the following $^{13}$C-NMR signals, relative to tetramethylsilane in CDCl$_3$: 205.1, 175.3, 172.3, 171.4, 170.4, 169.9, 169.6, 168.6, 158.7, 130.4 (2 carbons), 129.9, 114.0 (2 carbons), 81.5, 71.1, 67.6, 66.2, 63.2, 57.4, 55.4, 55.3, 54.7, 49.9, 49.5, 47.1, 42.5, 41.3, 38.6 (2 carbons), 35.4, 34.2, 34.0, 31.2, 27.9, 27.0, 25.1 (2 carbons), 24.9, 23.7, 22.9, 22.3, 21.0, 18.7, 16.9, 15.4, 14.9 (2 carbons), 11.7.

Didemnin B has the following $^{13}$C-NMR signals relative to tetramethylsilane in CDCl$_3$: 204.9, 174.0, 172.9, 172.4, 171.8, 171.3, 170.6, 169.7, 169.4, 168.4, 158.7, 130.3 (2 carbons) 130.1, 114.2 (2 carbons), 81.5, 70.5, 68.0, 66.5, 66.0, 57.7, 57.2, 56.7, 55.5, 55.3, 54.9, 49.6 (2 carbons), 47.0 (2 carbons), 41.4, 38.9, 38.7, 36.2, 34.0 (2 carbons), 31.3 (2 carbons), 28.4, 27.9, 27.2, 26.0, 24.9 (3 carbons) 23.8, 23.4, 21.4, 21.0, 20.3, 18.6, 16.9, 16.3, 15.2, 14.7, 11.7.

Infrared Spectra

The didemnins were dissolved in chloroform and examined in a Beckman IR-12 double beam spectrophotometer vs. a chloroform reference.

The spectrum of didemnin A is shown in FIG. 1. Peaks are observed at the following wavelengths:

| Band Frequency (Wave Number cm$^{-1}$) | Intensity (% T) |
| --- | --- |
| 3680 | 84 |
| 3600 | 82 sh |
| 3520 | 70 |
| 3340 | 54 |
| 3020 | 57 |
| 2970 | 39 |
| 2940 | 51 |
| 2880 | 60 |
| 2810 | 78 |
| 2460 | 82 |
| 1725 | 27.5 |
| 1650 | 23 |
| 1630 | 17 |
| 1605 | 64 |
| 1540 | 48 |
| 1505 | 31 |
| 1455 | 45 |
| 1445 | 43 |
| 1405 | 61 |
| 1380 | 59 |
| 1360 | 60 |
| 1335 | 60.5 |
| 1325 | 64 |
| 1310 | 60 sh |
| 1295 | 53 |
| 1265 | 51 |
| 1240 | 43 |
| 1195 | 63 sh |
| 1160 | 40 |
| 1110 | 62 |
| 1100 | 63.5 |
| 1080 | 66 sh |
| 1065 | 60 |
| 1030 | 71 |
| 1000 | 68 |
| 965 | 73 |
| 940 | 75 |
| 920 | 76 |
| 900 | 78 |
| 825 | 72 |
| 660 | 65 |
| 620 | 79 | sh = shoulder

Figure 2:
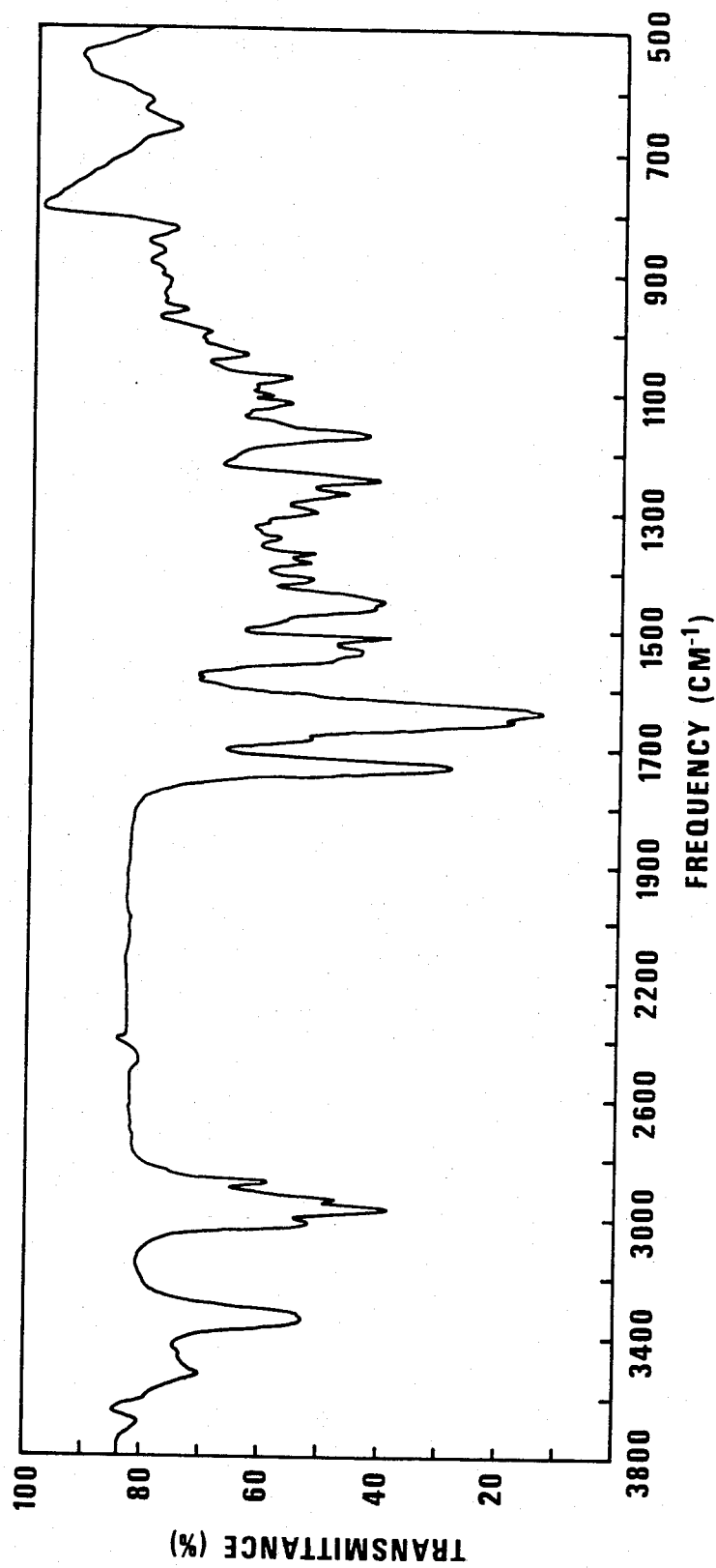

The spectrum of didemnin B is shown in FIG. 2. Peaks are observed at the following wavelengths:

| Band Frequency (Wave Number cm$^{-1}$) | Intensity (% T) |
| --- | --- |
| 3680 | 80 |
| 3600 | 79 |
| 3340 | 52.5 |
| 3020 | 51.5 |
| 2970 | 38 |
| 2940 | 47 |
| 2880 | 58 |
| 2460 | 81 |
| 1725 | 28 |
| 1650 | 17 |
| 1640 | 13 |
| 1630 | 15 sh |
| 1605 | 51 sh |
| 1540 | 44 |
| 1514 | 38.5 |
| 1465 | 41 |
| 1455 | 40 |
| 1415 | 52 |
| 1390 | 52.5 |
| 1370 | 52 |
| 1345 | 57.5 |
| 1300 | 51 |
| 1270 | 46 |
| 1250 | 40.5 |
| 1170 | 42 |
| 1120 | 56 |
| 1105 | 59 |
| 1075 | 56 |
| 1040 | 63.5 |
| 1000 | 70 |
| 965 | 73.5 |
| 940 | 77 |
| 910 | 76.5 |
| 900 | 78 |
| 865 | 78 |
| 830 | 76 |
| 660 | 75 |
| 615 | 80 | sh = shoulder

The infrared absorption spectrum for didemnin B when pressed into a KBr disc is as follows:

| Band Frequency | Intensity | Type |
| --- | --- | --- |
| 3672.9 | 73 | SH |
| 3562.9 | 50 | SH |
| 3501.2 | 40 | SH |
| 3479.0 | 38 | SH |

-continued

| Band Frequency | Intensity | Type |
|---|---|---|
| 3421.1 | 35 | SH |
| 3339.1 | 22 | BRD |
| 3214.7 | 56 | SH |
| 3065.2 | 60 | BRD |
| 3031.4 | 59 | BRD |
| 2962.0 | 12 | AVG |
| 2935.0 | 19 | AVG |
| 2875.2 | 33 | AVG |
| 2794.2 | 71 | SH |
| 2499.0 | 79 | BRD |
| 2063.1 | 80 | BRD |
| 1733.2 | 11 | AVG |
| 1663.8 | 6 | AVG |
| 1639.6 | 3 | AVG |
| 1583.7 | 49 | AVG |
| 1544.2 | 22 | AVG |
| 1514.3 | 13 | SH |
| 1488.2 | 33 | AVG |
| 1453.5 | 16 | AVG |
| 1413.0 | 31 | AVG |
| 1400.4 | 33 | BRD |
| 1386.0 | 25 | AVG |
| 1369.6 | 29 | AVG |
| 1342.6 | 32 | AVG |
| 1318.5 | 20 | AVG |
| 1305.0 | 24 | AVG |
| 1261.5 | 11 | AVG |
| 1250.0 | 14 | AVG |
| 1220.1 | 21 | AVG |
| 1169.0 | 14 | AVG |
| 1116.9 | 21 | SH |
| 1106.3 | 16 | AVG |
| 1092.8 | 17 | AVG |
| 1077.3 | 16 | AVG |
| 1033.9 | 19 | AVG |
| 1022.3 | 20 | SH |
| 966.4 | 54 | AVG |
| 938.4 | 63 | AVG |
| 924.0 | 63 | AVG |
| 862.2 | 58 | AVG |
| 802.4 | 20 | AVG |
| 755.2 | 60 | AVG |
| 720.4 | 57 | AVG |
| 704.1 | 58 | AVG |
| 650.0 | 54 | AVG |
| 615.3 | 53 | AVG |

Band Frequency in wavenumbers (cm$^{-1}$)
Intensity in percent transmittance (% T)
Data type in local peak region: BRD = Broad, AVG = Average, SH = Shoulder
This peak list is unedited

| % T | Frequency |
|---|---|
| 3 | 1639.5 |
| 6 | 1663.7 |
| 11 | 1733.1 |
| 11 | 1261.5 |
| 12 | 2962.0 |
| 13 | 1514.2 |
| 14 | 1250.0 |
| 14 | 1169.0 |
| 16 | 1453.5 |
| 25 Strongest Peaks | |
| % T | Frequency |
| 16 | 1106.2 |
| 16 | 1077.3 |
| 17 | 1092.7 |
| 19 | 2935.0 |
| 19 | 1033.8 |
| 20 | 1318.5 |
| 20 | 1022.2 |
| 20 | 802.3 |
| 21 | 1220.0 |
| 21 | 1116.8 |
| 22 | 3339.0 |
| 22 | 1544.1 |
| 24 | 1305.0 |
| 25 | 1386.0 |
| 29 | 1369.5 |
| 31 | 1413.0 |

Didemnin D has the following properties: mp 159°–161° C.; Rf 0.21 (3:1 chloroform:methanol); HPLC retention time 18.6 min (73:27 methanol:water); $[\alpha]^{25}_D$ −89.4° (c 4.37, CH$_2$Cl$_2$); FABMS major positive ions at m/z 71 (29% of base peak), 86 (100), 100 (91), 110 (16), 112 (18), 121 (39), 126 (45), 142 (38), 152 (38), 164 (51), 170 (16), 192 (29), 195 (15), 210 (17), 224 (16), 240 (11), 270 (9), 281 (10), 297 (17), 307 (17), 368 (11), 496 (6), 514 (8), 568 (9), 637 (11), 792 (34), 816 (33), 870 (9), 1038 (13), 1040 (20), 1240 (12), 1356 (14), 1368 (13), 1607 (M+H, 76). Hydrolysis, followed by derivatization and GC analysis, indicates the same amino acid composition as didemnin B with the addition of four moles of Glx (glutamic acid or glutamine). Addition of NaCl to the sample followed by HRFABMS analysis gave a value of m/z 1629.8330 for the resulting M+Na ion, corresponding to the expected molecular formula $C_{77}H_{118}N_{14}O_{23}$ for didemnin D ($\Delta$=5.7 mmu for M+Na).

Didemnin E has the following properties: mp 164°–166° C.; Rf 0.41 (3:1 chloroform:methanol); HPLC retention time 20.7 min (73:27 methanol:water); $[\alpha]^{25}_D$ −90.6° (c 7.06, CH$_2$Cl$_2$); FABMS major positive ions at m/z 70 (100% of base peak), 86 (41), 100 (34), 121 (19), 126 (19), 142 (24), 152 (17), 154 (11), 164 (25), 170 (21), 195 (7), 210 (8), 224 (7), 240 (7), 297 (9), 307 (6), 349 (2), 351 (2), 357 (2), 368 (3), 440 (4), 509 (5), 664 (12), 816 (5), 861 (3), 870 (4), 1040 (10), 1228 (7), 1240 (5), 1294 (3), 1368 (4), 1479 (M+H, 38).

Figure 3:
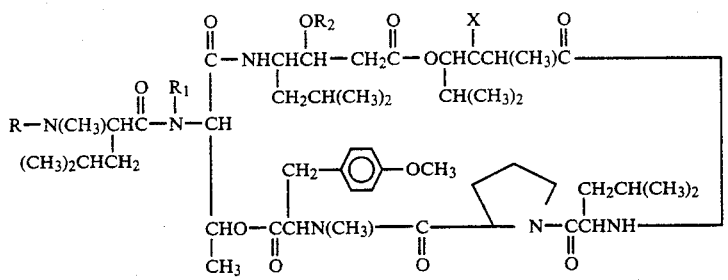
Figure 3:
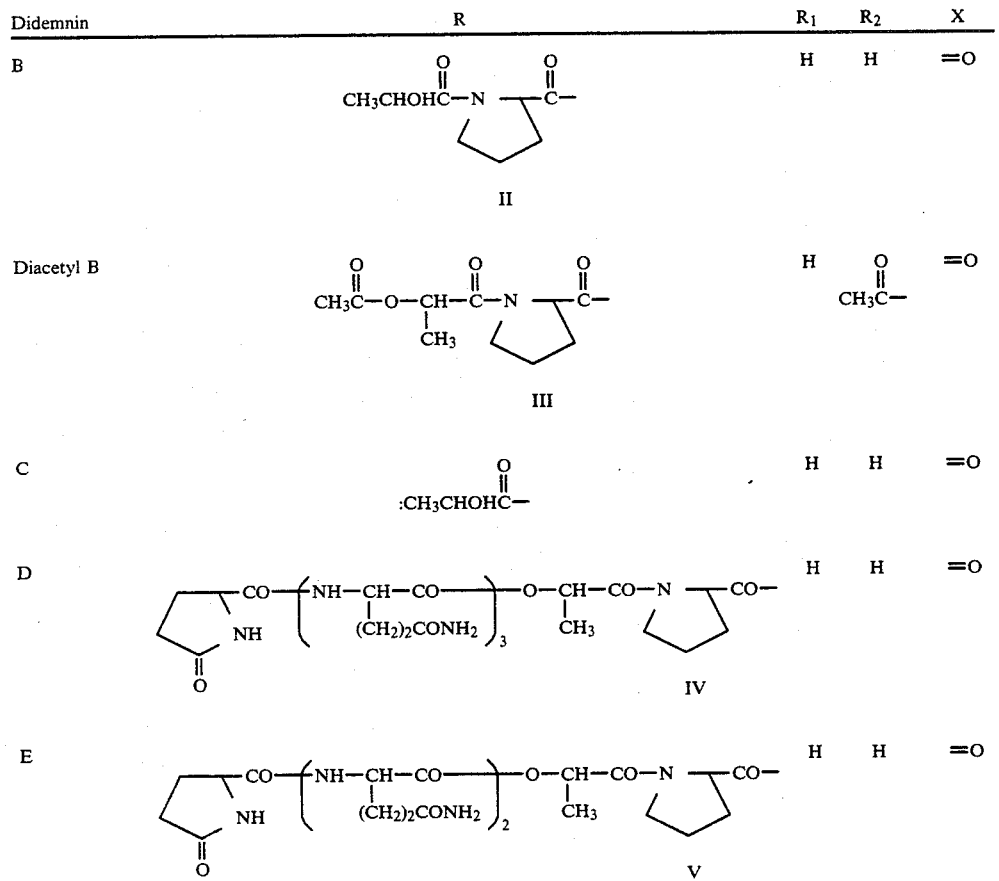
Figure 3:
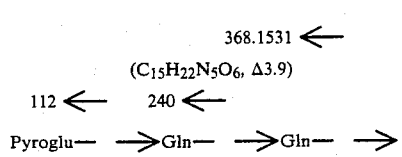

Hydrolysis, following by derivatization and GC analysis of the resulting trifluoroacetyl-n-butyl esters indicates the same amino acid composition as didemnin D with one less mole of Glx. HRFABMS gave a value of 1479.7930 daltons for the M+H ion, corresponding to the molecular formula $C_{72}H_{110}N_{12}O_{21}$ ($\Delta$=2.1 mmu) for didemnin E. Another important peak measured by HRFABMS was the ion at m/z 664.3256, corresponding to the fragment pyroGlu→Gln→Gln→Lac→Pro→MeLeu ($\Delta$=−5.0 mmu for $C_{30}H_{46}N_7O_{10}$). Other high resolution data and rationalization of the FAB mass spectra of didemnins D and E are shown in FIG. 3.

Antiviral Activity

The antiviral activities of didemnins A, B and C are shown in the following table. The test method is as follows:

Costar 96 well trays were seeded with 0.2 ml cell suspension and incubated at 37° for 24 hours. The medium was removed and the wells were treated with serial 2-fold dilutions of drug (150–1.5 μg/ml) in 0.05 ml. Diluted virus (0.05 ml) or medium (BME-3% fbs) was added to each well and the cultures were returned to 37°. After overnight incubation, the cells were stained with aqueous crystal violet (0.5%), and washed thoroughly. Drug concentrations resulting in 50% cell destruction (ID$_{50}$) were determined visually for those cultures infected with virus (antiviral) as well as those cultures serving as toxicity controls. Ratios are the cytotoxic concentration÷antiviral concentration.

The cells used for the herpes simplex virus (HSV) type 1 and type 2 were Vero. ML cells were used for the assays with coxsackie (COX) A21 and equine rhinovirus (ER).

|  | ID$_{50}$ (μg/ml) | | |
|---|---|---|---|
|  | A | B | C |
| RNA Viruses | | | |
| Toxicity-ML cells | 12 | <1.5 | 6 |
| Antiviral-COE virus | <1.5 | <1.5 | <1.5 |
| Ratio | >8 | ~1 | >4 |
| RNA Viruses | | | |
| Toxicity-ML cells | 12 | <1.5 | 6 |
| Antiviral-ER virus | <1.5 | <1.5 | <1.5 |
| Ratio | >8 | ~1 | >4 |
| DNA Viruses | | | |
| Toxicity-Vero cells | 25 | 25 | 50 |
| Antiviral-HSV-1 virus | <1.5 | <1.5 | <1.5 |
| Ratio | >17 | >17 | >33 |
| Toxicity-Vero cells | 25 | 25 | 50 |
| Antiviral-HSV-2 virus | <1.5 | <1.5 | <1.5 |
| Ratio | >17 | >17 | >33 |

Antiviral Activity-Agar Diffusion Plaque Inhibition Assay

These tests were performed by the methods described in the following published reference: (H. E. Renis, C. A. Hollowell, and G. E. Underwood, J. Med. Chem., Vol 10, pp 777–782 (1967)). Both DNA and RNA-containing viruses were used. The results are presented below as the zone of cytotoxicity (cell death)/zone of viral plaque inhibition for 50 μg of test compound.

| Didemnin | PR8 | COE | HA-1 | E.R. | HSV-1 | HSV-2 | VACC. |
|---|---|---|---|---|---|---|---|
| D | 4/0 | 4/0 | 4/0 | 4/4 | 4/0 | 4/0 | 4/0 |
| E | 4/0 | 4/0 | 4/0 | 4/4 | 4/0 | 4/0 | 4/0 |
| Diacetyl B | 3/0 | 3/3 | 1/0 | 2/4 | 3/4 | 3/4 | 3/4 |
| Diacetyl A | 0/0 | 0/3 | 0/4 | 0/4 | 1/4 | 1/4 | 1/4 |
| Methylene A | 0/0 | 0/2 | 0/4 | 0/4 | 0/4 | 0/4 | 0/4 |

PR-8 = Influenza (RNA)
COE = Coxsackie A-21 virus (RNA)
HA-1 = Parainfluenza 3 virus (RNA)
ER = Equine rhinovirus (RNA)
HSV-1 = Herpes simplex virus type I (DNA)
HVS-2 = Herpes simplex virus type II (DNA)
VACC = Vaccinia virus (DNA)

| | Vero[a] | Antiviral Activity - Virus Yield Assay | | | | | | | | | |
|---|---|---|---|---|---|---|---|---|---|---|---|
| | | HSV-1 | | HSV-2 | | VSV | | HA-1 | | COE | |
| DIDEMNIN | ID$_{50}$ | ED$_{90}$[b] | T[c] | ED$_{90}$ | T[c] | ED$_{90}$ | T[c] | ED$_{90}$ | T[c] | ED$_{90}$ | T[c] |
| D | 0.00195 | 2.835 | 0.00069 | 1.706 | 0.0011 | 9.3911 | 0.0002 | Inactive | — | 1.231 | 0.0016 |
| E | 0.0045 | 2.761 | 0.00162 | 2.461 | 0.0018 | 8.3835 | 0.0005 | Inactive | — | 1.2280 | 0.0036 |
| Diacetyl A | 1.1541 | 5.904 | 0.1955 | 5.586 | 0.2066 | 18.688 | 0.0618 | 1.3533 | 0.853 | 1.7918 | 0.6441 |
| Methylene A | 2.0792 | 8.399 | 0.2476 | 7.423 | 0.2801 | Inactive | — | 5.768 | 0.360 | 5.397 | 0.3852 |
| N—Acetyl A | 0.019 | 1.091 | 0.0175 | 0.456 | 0.0418 | 4.109 | 0.0047 | 0.316 | 0.605 | 0.498 | 0.0384 |
| Dihydro A | 15.1893 | Inactive | — | Inactive | — | Inactive | — | 17.248 | 0.881 | Inactive | — |
| B | 0.00103 | 2.084 | 0.0005 | 0.530 | 0.0019 | 6.671 | 0.0016 | 0.106 | 0.0097 | 0.7216 | 0.0014 |

[a]Cytotoxicity to Vero cells at 72 hr. after seeding (μg/ml).
[b]ED$_{90}$ is dose required to reduce virus yields by 90% (μg/ml).
[c]T is ID$_{50}$ (μg/ml) ÷ ED$_{90}$ (μg/ml).
HSV-I = Herpes simplex virus type I (DNA)
HSV-II = Herpes simplex virus type II (DNA)
VSV = Vesicular stomatitis virus
HA-1 = Parainfluenza 3 virus (RNA)
COE = Coxsackie A-21 virus (RNA)

Antileukemia Activity

Didemnins A-E inhibit the growth of L1210 mouse leukemia cells in vitro as shown in the following table.

The L1210 tube dilution assay is described in detail in a publication by L. H. Li, et al., Cancer Research 39:4816 (1979). ID$_{50}$ and ID$_{90}$ refer to the concentration of didemnins needed to inhibit cell growth by 50 and 90 percent, respectively.

| L1210 Tube Dilution Assay | | |
|---|---|---|
| Compound | ID$_{50}$ μg/ml | ID$_{90}$ μg/ml |
| Didemnin A | 0.031 | 0.056 |
| Diacetyldidemnin A | 0.015 | 0.052 |
| Methylene didemnin A | 0.0065 | 0.023 |
| N—acetyldidemnin A | 0.0024 | 0.007 |
| Dihydrodidemnin A | 0.52 | <1.0 |
| Didemnin B | 0.0022 | 0.0049 |
| Diacetyldidemnin B | 0.0016 | 0.0036 |
| Didemnin C | 0.011 | 0.019 |
| Didemnin D | 0.0065 | 0.016 |
| Didemnin E | 0.0051 | 0.013 |

Didemnins A and B were also active in vivo against P388 leukemia in mice. The P388 mouse leukemia test is described in detail in a publication by G. L. Neil, et al., Cancer Treatment Reports 63, 1971–1978 (1979). The results of three P388 mouse leukemia tests using different dosage schedules is shown below.

| In Vivo Testing of Didemnins Against P388 Leukemia | | | | |
|---|---|---|---|---|
| Compound[a] | Dose (μg/kg/ injection) | Median Survival Time[b] (day) | T/C (%) | Weight Change (g) |
| Didemnin A | 63 | 10.7 | 104 | +0.9 |
| | 125 | 11.9 | 115 | +1.4 |
| | 250 | 12.2 | 119 | +1.0 |
| | 500 | 13.2 | 129 | +0.9 |
| | 1000 | 16.2 | 158 | +0.3 |
| | 2000 | 16.0 | 155 | −0.2 |
| Didemnin B | 63 | 14.8 | 143 | +0.1 |
| | 125 | 14.0 | 136 | −0.6 |
| | 250 | 14.2 | 138 | −2.2 |
| | 500 | T[c] | T | −3.4 |
| | 1000 | T | T | T |
| | 2000 | T | T | T |

[a]Schedule of Injection: daily intraperitoneal injection for 9 days following tumor implantation.
[b]Median survival time of control animals = 10.3 days.
[c]Toxic.

| Compound | Dose (μg/kg/ injection) | Median Survival Time[b] (day) | T/C (%) | Weight Change (g) |
|---|---|---|---|---|
| Didemnin A | 250 | 11.1 | 109 | +1.7 |

-continued

| Compound | Dose (μg/kg/injection) | Median Survival Time[b] (day) | T/C (%) | Weight Change (g) |
|---|---|---|---|---|
|  | 500 | 12.1 | 118 | +1.6 |
|  | 1000 | 12.1 | 118 | +1.8 |
|  | 2000 | 12.4 | 121 | +2.0 |
|  | 4000 | 13.3 | 130 | +1.3 |
|  | 8000 | 14.3 | 140 | +0.8 |
| Didemnin B | 30 | 12.8 | 125 | +1.6 |
|  | 60 | 14.3 | 140 | +1.2 |
|  | 120 | 15.0 | 147 | +0.2 |
|  | 250 | 16.0 | 157 | −0.5 |
|  | 500 | 18.0 | 176 | −1.7 |
|  | 1000 | 20.3 | 199 | −3.8 |

[a]Schedule of injection: Intraperitoneal injection on Day 1, 5, and 9, following Tumor inoculation.
[b]Median survival time of Control (no drug) animals: 10.2 days.

| Compound | Optimal or Top Doses (mg/kg/injection)* | T/C (%) | Body Weight Change (g) |
|---|---|---|---|
| Didemnin B | 0.25 | 143 | +0.2 |
| Didemnin D | 2 | 123 | +1.0 |
|  | 1 | 119 | +1.7 |
| Didemnin E | 2 | 135 | −0.2 |
|  | 1 | 115 | +1.1 |
| Diacetyldidemnin A | 2 | 107 | +1.8 |
|  | 1 | 108 | +0.9 |
| N—Acetyldidemnin A | 2 | 133 | +0.2 |
|  | 1 | 127 | +0.2 |
| Methylene didemnin A | 2 | 111 | +0.4 |
|  | 1 | 107 | +1.3 |
| Diacetyldidemnin B | 2 | 111 | +1.3 |
|  | 1 | 111 | +1.1 |

*Schedule Q4D × 3

The administration of didemnins is useful prophylactically and therapeutically for treating viral infections. For example, pharmaceutical compositions containing the active ingredients are useful in prophylactic or therapeutic treatment of humans and animals infected or likely to be infected with viruses, e.g., hepatitis virus, rubella, rubeola, influenza, encephalitis viruses (i.e., arboviruses such as western or eastern equine encephalitis virus, Semliki Forest virus), herpes viruses (types 1 or 2 herpes simplex virus, cytomegalovirus, varicella-zoster and infectious bovine rhinotracheitis virus), rabies, enteroviruses (picornaviruses, echoviruses, coxsackie viruses), parainfluenza viruses, respiratory syncytial virus, sendai virus, poliomyelitis viruses, yellow fever, Epstein-Barr virus (infectious mononucleosis), small pox, Dengue virus, common cold virus (rhinoviruses, coronaviruses, etc.), adenoviruses, polyomaviruses, papovaviruses, RNA-tumar viruses (e.g., feline leukemia virus, avian leukosis virus, avian sarcoma viruses), B virus, aleutians disease of mink, arena viruses, blue tongue virus of sheep, bovine viral diarrhea-mucosal disease virus, canine distemper virus, canine hepatitis virus, canine herpesvirus, equine abortion virus, infectious equine anemia virus, fowl pox virus, hog cholera virus, Marek's disease, mink enteritis virus, Newcastle disease virus, porcine enterovirus, pseudorabies virus, foot and mouth disease virus, reoviruses, and all other viruses or diseases of viral origin (for example, slowly progressing diseases that may be of viral origin such as multiple sclerosis) that are sensitive to the antiviral action of the didemnins or nordidemnins.

The dosage administered will be dependent upon the identity of the viral infection, the type of host involved, its age, health, weight, kind of concurrent treatment, if any, frequency of treatment and therapeutic ratio.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally, 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Expressed in terms of concentration, an active ingredient can be present in the compositions of the present invention for localized use about the cutis, intranasally, pharyngolaryngeally, bronchially, broncholially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as a talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred, or by dry powder for insufflation.

The active ingredients can also be admixed in animal feed. The active ingredients can conveniently be prepared in the form of a food premix. The food premix can comprise an active ingredient in admixture with an edible pharmaceutical diluent such as starch, oatmeal, flour, calcium carbonate, talc, dried fish meal and the like nontoxic, orally acceptable pharmaceutical diluents. The prepared premix is then conveniently added to the regular feed.

For use as aerosols the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampuls, vials, segregated multiples of any of the foregoing, and other forms as herein described.

The active ingredients to be employed as anti-viral agents can be easily prepared in unit dosage form with the employment of pharmaceutical materials which themselves are available in the art and can be prepared by established procedures. The following preparations are illustrative of the preparation of the unit dosage forms of the present invention, but are not intended to be limiting.

EXAMPLE 13

Hard-Gelatin Capsules

One thousand two-piece hard gelatin capsules for oral use, each capsule containing 100 mg of a didemnin are prepared from the following types and amounts of ingredients:

a didemnin, micronized: 100 gm
Lactose: 100 gm
Corn Starch: 20 gm
Talc: 20 gm
Magnesium stearate: 2 gm The didemnin finely divided by means of an air micronizer, is added to the other finely powdered ingredients, mixed thoroughly and then encapsulated in the usual manner.

The foregoing capsules are useful for preventing or treating viral infection by the oral administration of one or two capsules one to four times a day.

Using the procedure above, capsules are similarly prepared containing didemnin in 50, 250 and 500 mg amounts by substituting 50 gm, 250 gm and 500 gm of didemnin for the 100 gm used above.

EXAMPLE 14

Soft Gelatin Capsules

One-piece soft gelatin capsules for oral use, each containing 250 mg of a didemnin (finely divided by means of an air micronizer), are prepared by first suspending the compound in 0.5 ml of corn oil to render the material capsulatable and then capsulating in the above manner.

The foregoing capsules are useful for preventing or treating viral infection by the oral administration of one or two capsules one to four times a day.

EXAMPLE 15

Tablets

One thousand tablets, each containing 500 mg of a didemnin are prepared from the following types and amounts of ingredients:

A didemnin, micronized: 500 gm
Lactose: 75 gm
Corn starch: 50 gm
Magnesium stearate: 4 gm
Light liquid petrolatum: 5 gm The didemnin finely divided by means of an air micronizer, is added to the other ingredients and then thoroughly mixed and slugged. The slugs are broken down by forcing through a Number Sixteen screen. The resulting granules are then compressed into tablets, each tablet containing 500 mg of the didemnin.

The foregoing tablets are useful for preventing or treating viral infection by the oral administration of one or two tablets one to four times a day.

Using the procedure above, tablets are similarly prepared containing a didemnin in 250 mg and 100 mg amounts by substituting 250 gm and 10 gm of a didemnin for the 500 gm used above.

EXAMPLE 16

Oral Suspension

One thousand ml of an aqueous suspension for oral use, containing in each teaspoonful (5 ml) dose, 500 mg of a didemnin, is prepared from the following types and amounts of ingredients:

A didemnin, micronized: 100 gm
Citric acid: 2 gm
Benzoic acid: 1 gm
Sucrose: 700 gm
Tragacanth: 5 gm
Lemon Oil: 2 gm
Deionized water, q.s. 1000 ml.

The citric acid, benzoic acid, sucrose, tragacanth and lemon oil are dispersed in sufficient water to make 850 ml of suspension. The didemnin, finely divided by means of an air micronizer, is stirred into the syrup until uniformly distributed. Sufficient water is added to make 1000 ml.

The composition so prepared is useful for preventing or treating viral infection at a dose of 1 tablespoonful (15 ml) three times a day.

EXAMPLE 17

A sterile aqueous suspension for parenteral injection, containing in 1 ml 300 mg of a didemnin, is prepared from the following types and amounts of ingredients:

A didemnin, micronized: 300 gm
Polysorbate 80: 5 gm
Methylparaben: 2.5 gm
Propylparaben: 0.17 gm
Water for injection, q.s. 1000 ml.

All the ingredients, except the didemnin, are dissolved in the water and the solution sterilized by filtration. To the sterile solution is added the sterilized didemnin, finely divided by means of an air micronizer, and the final suspension is filled into sterile vials and the vials sealed.

The composition so prepared is useful for preventing or treating viral infection at a dose of 1 milliliter (1M) three times a day.

EXAMPLE 18

Suppository, Rectal and Vaginal

One thousand suppositories, each weighing 2.5 gm and containing 150 mg of a didemnin are prepared from the following types and amounts of ingredients:

A didemnin, micronized: 150 gm
Propylene glycol: 150 gm
Polyethylene glycol #4000, q.s.: 2,500 gm The didemnin is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for preventing or treating viral infection.

EXAMPLE 19

Intranasal Suspension

One thousand ml of a sterile aqueous suspension for intranasal instillation, containing in each ml 150 mg of a didemnin, is prepared from the following types and amounts of ingredients:

A didemnin, micronized: 150 gm
Polysorbate 80: 5 gm
Methylparaben: 2.5 gm
Propylparaben: 0.17 gm
Deionized water, q.s. 1000 ml.

All the ingredients, except the didemnin, are dissolved in the water and the solution sterilized by filtration. To the sterile solution is added the sterilized didemnin, finely divided by means of an air micronizer, and the final suspension is aseptically filled into sterile containers.

The composition so prepared is useful for preventing or treating viral infection by intranasal instillation of 0.2 to 0.5 ml given one to four times per day.

EXAMPLE 20

Animal Feed

One thousand grams of feed premix is prepared from the following types and amounts of ingredients:

A didemnin: 20 gm
Soybean meal: 400 gm
Fish meal: 400 gm
Wheat germ oil: 50 gm
Sorghum molasses: 130 gm The ingredients are mixed together and pressed into pellets.

The premix can be fed directly to laboratory animals, i.e., rats and mice, for preventing or treating viral infection.

For larger animals the premix can be added to the animal's regular feed in an amount calculated to give the desired dose of didemnin. For example, one part of premix is added to 2.5 parts of a cat's regular feed to provide the desired dose of 200 mg/kg/day for a cat of 2.5 kg.

An active ingredient can also be present, as shown in Examples 12–15 in the undiluted pure form for use locally about the cutis, intranasally, pharyngolaryngeally, bronchially, broncholially or orally.

EXAMPLE 21

Powder

Five hundred grams of a didemnin in bulk form is finely divided by means of an air micronizer. The micronized powder is placed in a shaker-type container.

The foregoing composition is useful for preventing or treating viral infection at localized sites by applying the powder one to four times per day.

EXAMPLE 22

Oral Powder

One thousand grams of a didemnin in bulk form is finely divided by means of an air micronizer. The micronized powder is divided into individual doses of 250 mg and packaged.

The foregoing powders are useful for preventing or treating viral infection by the oral administration of one or two powders suspended in a glass of water, one to four times per day.

EXAMPLE 23

Insufflation

One thousand grams of a didemnin in bulk form is finely divided by means of an air micronizer.

The foregoing composition is useful for preventing or treating viral infection by the inhalation of 30 to 75 mg one to four times per day.

EXAMPLE 24

Hard Gelatin Capsules

One thousand two-piece hard gelatin capsules for oral use, each capsule containing 100 mg of a didemnin.

The didemnin is finely divided by means of an air micronizer and encapsulated in the usual manner.

The foregoing capsules are useful for preventing or treating viral infection by the oral administration of one or two capsules one to four times a day.

Using the procedure above, capsules are similarly prepared containing didemnin in 50, 250 and 500 mg amounts by substituting 50 gm, 250 gm and 500 gm of a didemnin for the 100 gm used above.

Data show that the structures for didemnin A, B and C can be shown as follows:

```
R—>MeLeu—>Thr—>Sta—>O—CHCOCHCO ⎤
                  |         |    |
                  O     (CH3)2CH  CH3
                  |
                 Me2Tyr <—Pro<—Leu <—
```

Didemnin A: R=H
Didemnin B: R=CH$_3$CHOHCO→Pro→
Didemnin C: R=CH$_3$CHOHCO→

Where MeLeu = →N—CH—CO→
             |    |
             CH$_3$  CH$_2$CH(CH$_3$)$_2$ Thr = →NH—CH—CO→
          |
          CHCH$_3$
          |

Sta = →NH—CH—CHOH—CH$_2$—CO→
           |
           CH$_2$CH(CH$_3$)$_2$

Me$_2$Tyr = →N—CH—CO→
            |    |
            CH$_3$  CH$_2$
                 |
                (C$_6$H$_4$)
                 |
                 OCH$_3$

Pro = →N—CH—CO→
       |    |
       CH$_2$  CH$_2$
        \  /
         CH$_2$

Leu = →NH—CH—CO→
           |
           CH$_2$CH(CH$_3$)$_2$

CHART I

Didemnin Structures

I

| Didemnin | R | R$_1$ | R$_2$ | X |
|---|---|---|---|---|
| A | H | H | H | =O |
| N—Acetyl A | CH$_3$C(=O)— | H | H | =O |
| Diacetyl A | CH$_3$C(=O)— | H | CH$_3$C(=O)— | =O |
| Dihydro A | H | H | H | H$_2$OH |
| Methylene A | —CH$_2$— | | H | =O |

CHART I-continued
Didemnin Structures

+ FABMS Fragmentations for Didemnins E (and D)

FORMULAS
-continued

V:
$$\text{pyrrolidone-CO-[NH-CH(CH}_2)_2\text{CONH}_2\text{)-CO]}_2\text{-O-CH(CH}_3\text{)-CO-N(pyrrolidine)-CO-}$$

VI:
$$\text{HN-(ring)-C(=O)-}$$

I claim:

1. A didemnin of the Formula I

I:
$$\text{R-N(CH}_3\text{)CHC(=O)-N(R}_1\text{)-}$$
with (CH$_3$)$_2$CHCH$_2$ branch, and continuing:
—C(=O)—NHCHCH—CH$_2$C(=O)—OCHCC(CH$_3$)C(=O)— with OR$_2$, X substituents, CH$_2$CH(CH$_3$)$_2$, CH(CH$_3$)$_2$ branches
with -CH, CHO-CH(CH$_3$)-, CH$_2$-C$_6$H$_4$-OCH$_3$, pyrrolidine ring, CH$_2$CH(CH$_3$)$_2$, CCHNH groups wherein R is
 (a) hydrogen,
 (b) —COCH$_3$,
 (c) a side chain of Formula II,

II:
$$\text{CH}_3\text{CHOHC(=O)-N(pyrrolidine)-C(=O)-}$$

(d) a side chain of Formula III,

III:
$$\text{CH}_3\text{C(=O)-O-CH(CH}_3\text{)-C(=O)-N(pyrrolidine)-C(=O)-}$$

(e) CH$_3$CHOHC(O)—,
(f) a side chain of Formula IV,

IV:
$$\text{pyrrolidone-CO-[NH-CH((CH}_2)_2\text{CONH}_2\text{)-CO]}_3\text{-O-}$$
$$\text{-CH(CH}_3\text{)-CO-N(pyrrolidine)-CO-}$$

(g) a side chain of Formula V,

V:
$$\text{pyrrolidone-CO-[NH-CH((CH}_2)_2\text{CONH}_2\text{)-CO]}_2\text{-O-}$$
$$\text{-CH(CH}_3\text{)-CO-N(pyrrolidine)-CO-}$$

(h) CH$_3$CH$_2$(CO)—,
(i) (CH$_3$)$_2$CHCH$_2$CH(NH$_2$)C(O)—, or
(j) a side chain of the formula VI,

VI:
$$\text{HN-(ring)-C(=O)-}$$

wherein R$_1$ is hydrogen; or R and R$_1$ taken together form methylene (—CH$_2$—); wherein R$_2$ is
 (a) hydrogen, or
 (b) —COCH$_3$; and
wherein X is
 (a) =O, or
 (b) H, —OH,
or an acylate thereof.

2. Antibiotic didemnin A, a compound of claim 1, wherein R, R$_1$, and R$_2$ are hydrogen and X is =O, or a pharmaceutically acceptable salt thereof.

3. Antibiotic didemnin B, a compound of claim 1, wherein R$_1$ and R$_2$ are hydrogen, R is a Formula II substituent —COCH$_3$, and X is =O, or a pharmaceutically acceptable salt thereof.

4. Antibiotic didemnin C, a compound of claim 1, wherein R is CH$_3$CHOHC(O), R$_1$ and R$_2$ are hydrogen, and X is =O, or a pharmaceutically acceptable salt thereof.

5. N-acetyldidemnin A, a compound of claim 1, wherein R is —COCH$_3$, R$_1$ and R$_2$ are hydrogen, and X is =O; or a pharmaceutically acceptable salt thereof.

6. Diacetyldidemnin A, a compound of claim 1, wherein R and R$_2$ are —COCH$_3$, R$_1$ is hydrogen, and X is =O; or a pharmaceutically acceptable salt thereof.

7. Dihydrodidemnin A, a compound of claim 1 wherein R, R$_1$, and R$_2$ are hydrogen and X is H, OH; or a pharmaceutically acceptable salt thereof.

8. Methylene didemnin A, a compound of claim 1, wherein R and R$_1$ form —CH$_2$—, R$_2$ is hydrogen, and X is =O.

9. Diacetyldidemnin B, a compound of claim 1, wherein R is a Formula III substituent, R$_1$ is hydrogen, $R_2$ is $-COCH_3$, and X is $=O$; or a pharmaceutically acceptable salt thereof.

10. Didemnin D, a compound of claim 1, wherein R is a Formula IV substituent, $R_1$ and $R_2$ are hydrogen, and X is $=O$; or a pharmaceutically acceptable salt thereof.

11. Didemnin E, a compound of claim 1, wherein R is a Formula V substituent, $R_1$ and $R_2$ are hydrogen, and X is $=O$; or a pharmaceutically acceptable salt thereof.

12. N-Propionyl-Didemnin A, a compound of claim 1, wherein R is $CH_3CH_2C(O)-$, $R_1$ and $R_2$ are hydrogen, and X is $=O$; or a pharmaceutically acceptable salt thereof.

13. N-(L)-Leucyl Didemnin A, a compound of claim 1, wherein R is $(CH_3)_2CHCH_2CH(NH_2)(Co)-$, $R_1$ and $R_2$ are hydrogen and X is $=O$; or a pharmaceutically acceptable salt thereof.

14. N-(L)-Prolyl-Didemnin A, a compound of claim 1, wherein R is a formula VI substituent, $R_1$ and $R_2$ are hydrogen, and X is $=O$, or a pharmaceutically acceptable salt thereof.

* * * * *

UNITED STATES PATENT OFFICE
CERTIFICATE OF CORRECTION

Patent No. 4,493,796  Dated 15 January 1985

Inventor(s) K.L. Rinehart, Jr.

It is certified that error appears in the above-identified patent and that said Letters Patent are hereby corrected as shown below:

Column 12, line 61 reads: "didemnin B"; should read: --didemnin C--.

Signed and Sealed this

Twenty-second Day of October 1985

[SEAL]

Attest:

DONALD J. QUIGG

Attesting Officer

Commissioner of Patents and Trademarks—Designate

UNITED STATES PATENT AND TRADEMARK OFFICE
CERTIFICATE OF CORRECTION

PATENT NO. : 4,493,796
DATED : January 15, 1985
INVENTOR(S) : Rinehart, Jr.

It is certified that error appears in the above-indentified patent and that said Letters Patent is hereby corrected as shown below:

Column 1, line 11, insert the following:

"This invention was made with Government support under Grant No. AI04769 awarded by the National Institutes of Health. The Government has certain rights in the invention."

Signed and Sealed this

Eleventh Day of July, 1995

*Attest:*

BRUCE LEHMAN

*Attesting Officer*     *Commissioner of Patents and Trademarks*